United States Patent [19]

Totakura et al.

[11] Patent Number: 5,795,584
[45] Date of Patent: Aug. 18, 1998

[54] POST-SURGICAL ANTI-ADHESION DEVICE

[75] Inventors: Nagabhushanam Totakura, Norwalk; Ross R. Muth, Brookfield; Roy D. Gravener, Fairfield; Matthew Hain, New Haven; Ilya S. Koyfman, Orange, all of Conn.

[73] Assignee: United States Surgical Corporation, Norwalk, Conn.

[21] Appl. No.: 385,007

[22] Filed: Feb. 7, 1995

Related U.S. Application Data

[60] Division of Ser. No. 153,336, Nov. 16, 1993, abandoned, which is a continuation-in-part of Ser. No. 9,726, Jan. 27, 1993, abandoned.

[51] Int. Cl.$^6$ ............................................. A61K 9/70
[52] U.S. Cl. ..................... 424/426; 424/78.37; 424/444; 424/486; 602/46; 602/904
[58] Field of Search ................ 602/904, 43–48, 602/52; 604/890.1; 728/899; 424/426, 444, 486, 78.37; 523/112, 113

[56] References Cited

U.S. PATENT DOCUMENTS

| | | | |
|---|---|---|---|
| 974,294 | 11/1910 | Pond | 604/304 |
| 2,465,357 | 3/1949 | Correll | 424/426 |
| 3,276,448 | 10/1966 | Kronenthal | 606/151 |
| 3,739,773 | 6/1973 | Schmitt et al. | 606/62 |
| 3,773,919 | 11/1973 | Boswell et al. | 424/19 |
| 3,875,937 | 4/1975 | Schmitt et al. | 604/307 |
| 3,937,223 | 2/1976 | Roth | 602/45 |
| 3,960,152 | 6/1976 | Augurt et al. | 606/230 |

(List continued on next page.)

FOREIGN PATENT DOCUMENTS

| | | |
|---|---|---|
| 0262890 | 4/1988 | European Pat. Off. . |
| 0325195 | 7/1989 | European Pat. Off. . |
| 0334046 | 9/1989 | European Pat. Off. . |
| 0372969 | 6/1990 | European Pat. Off. . |
| 0427185 | 5/1991 | European Pat. Off. . |
| 2222954 | 3/1990 | United Kingdom . |
| WO 8600912 | 2/1986 | WIPO . |
| WO 8804557 | 6/1988 | WIPO . |
| WO 92/10218 | 6/1992 | WIPO . |

OTHER PUBLICATIONS

Ethisorb® Pledgets (Product literature) 1992.

Nakamura et al., Bioabsorbable Non–Woven Fabric for Surgery, Medical Textiles for Implantation, Planck, Danner and Renardy Eds. pp. 329–332 (1990).

Nakamura et al., New Bioabsorbable Pledgets and Non-woven Fabrics Made from Polyglycolide (PGA) for Pulmonary Surgery: Clinical Experience, Thorac. cardiovasc. Surgn. 38 (1990) 81–85.

(List continued on next page.)

*Primary Examiner*—Neil S. Levy

[57] ABSTRACT

Surgical adhesion barriers and methods of using such surgical adhesion barriers are provided. Surgical adhesion barriers according to the present invention have at least one layer of a bioabsorbable material comprising copolymers and/or block copolymers derived from trimethylene carbonate. Alternatively, a multilayer surgical structure having one or more bioabsorbable layers superimposed on a nonabsorbable layer is useful for minimizing or preventing formation of fibrous adhesions between a healing trauma site and adjacent surrounding tissue. Alternatively, a bioabsorbable non-woven fabric in adherent contact with at least one bioabsorbable layer of foam, film, mesh, web or woven fabric is also provided. One or more medicinal agents may be interposed between or disposed within any of the aforementioned layers.

5 Claims, 1 Drawing Sheet

U.S. PATENT DOCUMENTS

| | | |
|---|---|---|
| 3,988,411 | 10/1976 | Capozza .................................. 264/184 |
| 4,033,938 | 7/1977 | Augurt et al. ........................... 528/354 |
| 4,074,366 | 2/1978 | Capozza .................................... 623/1 |
| 4,074,713 | 2/1978 | Capozza .................................... 606/77 |
| 4,128,612 | 12/1978 | Roth ......................................... 264/126 |
| 4,135,622 | 1/1979 | Glick ...................................... 206/63.3 |
| 4,186,448 | 2/1980 | Brekke ...................................... 623/16 |
| 4,373,519 | 2/1983 | Errede et al. ............................. 502/43 |
| 4,429,080 | 1/1984 | Casey et al. .............................. 525/45 |
| 4,500,676 | 2/1985 | Balazs et al. ........................ 428/425.1 |
| 4,520,821 | 6/1985 | Schmidt et al. ......................... 606/151 |
| 4,532,134 | 7/1985 | Malette et al. ............................ 514/55 |
| 4,549,545 | 10/1985 | Levy ........................................ 606/228 |
| 4,572,906 | 2/1986 | Sparkes et al. ........................... 514/21 |
| 4,578,067 | 3/1986 | Cruz, Jr. .................................... 602/50 |
| 4,594,407 | 6/1986 | Nyilas et al. ............................ 528/272 |
| 4,603,695 | 8/1986 | Ikada et al. .............................. 128/334 |
| 4,633,873 | 1/1987 | Dumican et al. ........................ 606/151 |
| 4,655,221 | 4/1987 | Devereux ................................. 606/151 |
| 4,670,286 | 6/1987 | Nyilas et al. ................................ 427/2 |
| 4,674,488 | 6/1987 | Nashef et al. ............................. 606/76 |
| 4,693,720 | 9/1987 | Scharnberg et al. ...................... 623/11 |
| 4,803,078 | 2/1989 | Sakai ....................................... 424/445 |
| 4,838,884 | 6/1989 | Dumican et al. ........................ 604/364 |
| 4,840,626 | 6/1989 | Linsky et al. ............................ 604/364 |
| 4,865,031 | 9/1989 | O'Keeffe ................................. 606/151 |
| 4,882,162 | 11/1989 | Ikada et al. .............................. 424/444 |
| 4,891,263 | 1/1990 | Kotliar et al. ........................... 428/225 |
| 4,906,463 | 3/1990 | Cleary et al. ............................ 424/449 |
| 4,911,926 | 3/1990 | Henry et al. ......................... 424/78.06 |
| 4,916,193 | 4/1990 | Tang et al. .............................. 525/413 |
| 4,916,207 | 4/1990 | Royle, Jr. et al. ....................... 528/370 |
| 4,920,203 | 4/1990 | Tang et al. .............................. 525/409 |
| 4,942,875 | 7/1990 | Blavacek et al. ........................ 606/230 |
| 4,950,483 | 8/1990 | Ksander et al. ......................... 424/422 |
| 4,994,277 | 2/1991 | Higham et al. .......................... 424/443 |
| 5,002,551 | 3/1991 | Linsky et al. ............................ 606/151 |
| 5,007,916 | 4/1991 | Linsky et al. ............................ 606/151 |
| 5,011,692 | 4/1991 | Fujioka et al. .......................... 424/426 |
| 5,019,393 | 5/1991 | Ito et al. .................................. 424/423 |
| 5,035,893 | 7/1991 | Shioya et al. ........................... 424/447 |
| 5,041,138 | 8/1991 | Vacanti et al. ............................ 623/16 |
| 5,061,281 | 10/1991 | Mares et al. ............................... 523/11 |
| 5,066,772 | 11/1991 | Tang et al. .............................. 528/354 |
| 5,080,665 | 1/1992 | Jarrett et al. ............................ 606/219 |
| 5,080,893 | 1/1992 | Goldberg et al. ......................... 574/57 |
| 5,092,884 | 3/1992 | Devereux et al. .......................... 623/11 |
| 5,093,319 | 3/1992 | Higham et al. ............................ 514/55 |
| 5,102,983 | 4/1992 | Kennedy ................................. 528/354 |
| 5,120,802 | 6/1992 | Mares et al. ............................. 525/415 |
| 5,126,140 | 6/1992 | Ito et al. .................................. 424/423 |
| 5,126,141 | 6/1992 | Henry ...................................... 424/423 |
| 5,145,945 | 9/1992 | Tang et al. .............................. 528/370 |
| 5,152,781 | 10/1992 | Tang et al. .............................. 606/230 |
| 5,185,408 | 2/1993 | Tang et al. .............................. 528/415 |
| 5,236,444 | 8/1993 | Muth et al. .............................. 606/230 |
| 5,236,447 | 8/1993 | Kubo et al. ................................ 623/1 |

OTHER PUBLICATIONS

Nakamura et al., Clinical Applications of Bioabsorbable PGA Sheets for Suture Reinforcement and Use as Artificial Pleura, Japan Lung Surgery Journal 40: 10.8 (1826) 1992 w/translation.

Montz et al., Inability of Polyglycolic Acid Mesh to Inhibit Immediate Post–Radical Pelvic Surgery Adhesions, Gynecologic Oncology, 38, 230–233 (1990).

Williams/Gilding, Biocompatibility of Clinical Implant Materials, vol. 11, pp. 210–232, 1981.

Malm et al., Prevention of postoperative pericardial adhesions by closure of the pericardium with absorbable polymer patches; The Journal of Thoracic and Cardiovascular Surgery; 104, 3, pp. 600–607, (1992).

Yemini et al., Prevention of Reformation of Pelvic Adhesions by "Barrier" Methods, Int. J. Fertil., 29(3), 1984, pp. 194–196.

Ellis, The Cause and Prevention of Postoperative Intraperitoneal Adhesions, Surgery, Gynecology & Obstetrics, vol. 133, 1971, pp. 497–511.

Goldberg et al., Prevention With the Use of Hydrophilic Polymer Coatings, Arch. Surg., vol. 115, 1980, pp. 776–780.

LaRocca, The Laminectomy Membrane, The Journal of Bone and Joint Surgery, vol. 56 B, No. 3, 545–550, 1974.

FIG. 1

POST-SURGICAL ANTI-ADHESION DEVICE

This is a divisional, of U.S. application Ser. No. 08/153,336 filed Nov. 16, 1993, now abandoned, which is a continuation-in-part of U.S. application Ser. No. 08/009,726 filed Jan. 27, 1993, now abandoned.

BACKGROUND OF THE INVENTION

1. Field of the Invention

The present invention relates to minimization and/or prevention of post-surgical adhesions and more particularly, to devices and methods for preventing the formation of such adhesions between a healing trauma site and adjacent surrounding tissue.

2. Description of Related Art

Injury, surgical incision or abrasion to the peritoneum, pleural or abdominal cavity results in an outpouring of a serosanguinous exudate. The exudate subsequently coagulates, producing fibrinous bands between abutting surfaces which can become organized by fibroblast proliferation to become collagenous adhesions. Adhesions are also known to form at bone fracture sites where jagged, irregular bone edges form in the area of the fracture. Bony spurs promote the growth of fibrous adhesions between the bone fracture surface and surrounding tissue.

Adhesion formation following surgery or trauma is generally considered to be undesirable. For example, adhesions that form in relation to intestinal surgery, e.g., bowel resection, hernia repair, etc. may cause obstruction of the intestine. Adhesions that form near the bone fracture site may reduce or hinder the normal movement of the area of repair by restricting the natural movement of tendons over the adjacent bone. Adhesions may also form in the vicinity of nerves and disrupt nerve transmissions with a resultant diminution of sensory or motor function.

Various methods and substances have been used in the hope of preventing post-operative adhesions. Certain drugs and surfactants have been suggested. For example, U.S. Pat. No. 4,911,926 is directed to adhesion prevention by application of aqueous and non-aqueous compositions of a polyoxyalkylene block copolymer to injured areas of the peritoneal or pleural cavity or organs situated therein subsequent to surgical injury.

Another approach to adhesion prevention involves application of a physical barrier at the area of surgical injury. U.S. Pat. No. 4,674,488 is directed to interposing a barrier layer of soft biological tissue, such as collagen, collagen-fabric films, collagen membranes, or reconstituted collagen or Dacron® mesh, at the interface of a bone fracture and the surrounding tissue. U.S. Pat. No. 4,603,695 is directed to a molded polymeric material for preventing adhesion of vital tissues. The polymeric material is made of a biodegradable and absorbable polymer such as certain polyesters, collagen, amino acid polymers and chitin and may be placed where there is a possibility of adhesion setting in.

Other materials have also been used to form physical barriers in an attempt to prevent adhesions, including silicone elastomers, gelatin films and knit fabrics of oxidized regenerated cellulose (hereinafter ORC). In some cases, it is suggested that heparin, heparinoid, or hexuronyl hexosaminoglycan be incorporated into a matrix of ORC fabric or other matrices of hyaluronic acid, cross-linked and uncross-linked collagen webs, synthetic resorbable polymers, gelatin films, absorbable gel films, oxidized cellulose fabrics and films which are fabricated into a form that is said to be drapable, conformable and adherent to body organs and substantially absorbable within 30 days. See, e.g., U.S. Pat. No. 4,840,626 or EPA Pub. No. 0 262 890 or EPA Pub. No. 0 372 969.

Physical barriers are also used to cover and protect wound sites. PCT/US91/08972 is directed to a surgical article having a bioabsorbable fibrous matrix in a laminar relationship with a bioabsorbable cell barrier sheet. U.S. Pat. No. 5,092,884 and EPA Pub. No. 0 334 046 are directed to a surgical composite structure having absorbable and non-absorbable components which may be useful for repairing anatomical defects, e.g., preventing hernia formation in an infected area. The nonabsorbable portion of the composite acts as a reinforcement material. Ingrowth of natural tissue is said to be enhanced by controlled degradation of the absorbable portion. U.S. Pat. No. 5,035,893 relates to a wound covering composition having a sheet of biopolymeric material and a film of polyurethane resin. An antibacterial agent may be provided between the polyurethane film and the sheet of biopolymeric material, thereby forming a three-layer wound covering material. With the cure of the wound, it is said that the biopolymeric material is taken in a living tissue and the polyurethane film can be peeled off from the sheet without hurting the surface of a wound.

SUMMARY OF THE INVENTION

The present invention provides surgical adhesion barriers and methods of using surgical adhesion barriers which have at least one layer of bioabsorbable material. The bioabsorbable material comprises copolymers, block copolymers or blends thereof. The copolymers comprises carbonates and at least one other bioabsorbable polymer forming material. The block copolymers comprise at least one block comprising trimethylene carbonate. In one embodiment the block copolymer comprises a first block formed from a copolymer having a predominant amount of trimethylene carbonate and a second block formed from a copolymer having a predominant amount of lactide.

In another embodiment, the present invention provides a multilayer surgical structure having one bioabsorbable layer affixed to a non-absorbable layer. Both the absorbable and the non-absorbable layer may be fashioned from mesh, web, woven fabric, non-woven fabric, porous film, non-porous film or foam. The structure is made by superimposing a layer of bioabsorbable material on a non-absorbable layer. In alternative embodiments subsequent bioabsorbable layers can be added. Additionally, one or more medicinal agents can be interposed between any of the aforementioned layers.

In another embodiment, the present invention provides a multilayer surgical structure having a bioabsorbable non-woven fabric in adherent contact with one or more bioabsorbable layers which may be in the form of film, foam, mesh, web or woven fabric.

The surgical adhesion barrier or multilayer surgical structure is flexible, resilient and conformable to various shapes such as body organs and tissues. During surgery, a surgical adhesion barrier according to the present invention is positioned at the area of injury to prevent adhesions as desired. Likewise, a multilayer surgical structure according to the present invention having absorbable and non-absorbable layers is positioned at the area of injury to prevent adhesions as desired. In the case of a multilayer adhesion barrier, the nonabsorbable layer is preferably positioned adjacent to the area of injury and the bioabsorbable layer(s) face away from the injury. As the bioabsorbable layer is absorbed, any adhesions which may have attached to the bioabsorbable layer lose their support and fall free of the injury site.

In yet another embodiment, the multilayer surgical structure incorporates a plurality of bioabsorbable layers which bioabsorb at different rates. Each layer of bioabsorbable material is absorbed over time, thus exposing and releasing any medicinal agents which may be contained between layers.

The structures of the present invention may find application for open general surgery or less invasive surgical techniques such as endoscopic surgery, or both.

DETAILED DESCRIPTION OF THE INVENTION

A surgical adhesion barrier according to the present invention prevents formation of surgical adhesions at a surgical wound by interposing a unique bioabsorbable barrier between the surgical wound and surrounding tissue.

In accordance with one aspect of the present invention, a surgical adhesion barrier is constructed from a single layer of bioabsorbable material. The bioabsorbable material is made of copolymers of carbonates and at least one other bioabsorbable polymer forming material. Carbonates which are useful according to the present invention may be represented by the structural units of formula , wherein R is a carbon atom and n preferably ranges from about 1 to about 8. Examples of suitable carbonates include dimethylene carbonate, trimethylene carbonate, tetramethylene carbonate, pentamethylene carbonate, hexamethylene carbonate and the like.

Suitable bioabsorbable polymer forming materials which maybe copolymerized with a suitable carbonate include materials capable of forming hydrolyzable polyesters. Suitable materials capable of forming hydrolyzable polyesters include glycolide and lactide; hydroxyacids such as glycolic acid, lactic acid, hydroxy butyric acids, and hydroxyvaleric acids; lactones such as β-propio-lactone, ∂-caprolactone, ε-caprolactone, methyl-caprolactone, dioxanone, p-dioxanone, methyl-p-dioxanone, dimethyl-p-dioxanone, and β-malolactone; and polyalkylene oxides such as polyoxyethylene glycol and polyoxypropylene glycol; and mixtures, blends, and copolymers thereof.

The single layer surgical adhesion barrier embodiment of the present invention preferably comprises a bioabsorbable copolymer of trimethylene carbonate and glycolide, the trimethylene carbonate being present in a predominant amount. A "predominant amount", as used herein, is an amount greater than 50 mole percent of a composition. Preferably, the concentration of glycolide and trimethylene carbonate in this embodiment of the present invention is about 20 and 80 mole percent, respectively.

Suitable single layer surgical adhesion barriers of the present invention can also be fabricated from block copolymers having one or more "A" blocks comprising a carbonate as described above and a bioabsorbable polymer forming material as described above, and one or more "B" blocks comprising a bioabsorbable polymer forming material as described above. Preferably the "A" blocks are present in amounts ranging from about 10% to about 90% and the "B" blocks are present in amounts ranging from about 10% to about 90%. In a still more preferred embodiment, the "A" blocks are present in an amount ranging from about 15 weight percent to about 85 weight percent and the "B" blocks present in an amount ranging from about 15 weight percent to about 85 weight percent. Most preferably, the "A" and "B" blocks are present in amounts of about 50 percent by weight each.

Suitable "A" blocks include a predominant amount, i.e., greater than about 50 mole percent, of trimethylene carbonate. Preferably the trimethylene carbonate ranges from about 75 mole percent to about 95 mole percent. A more preferable concentration of trimethylene carbonate ranges from about 80 mole percent to about 90 mole percent and is most preferably about 80 mole percent. The trimethylene carbonate may be copolymerized with any monomer which provides an absorbable copolymer to form the "A" block. Such monomers include but are not limited to glycolide, lactide, dioxanone, epsilon caprolactone, with glycolide being preferred.

Suitable "B" blocks include a predominant amount of lactide (i.e., greater than about 50 mole percent) but preferably ranging from about 75 mole percent to about 95 mole percent. A more preferable concentration of lactide ranges from about 80 mole percent to about 90 mole percent and is most preferably about 80 mole percent. The lactide may be copolymerized with any monomer such that an absorbable copolymer is provided to form the "B" block. Such monomers include but are not limited to glycolide, dioxanone, and epsilon caprolactone, trimethylene carbonate, with glycolide being preferred.

An adhesion barrier constructed from a single layer of bioabsorbable material may be in the form of mesh, web, woven fabric, non-woven fabric, foam, matrix or, most preferably, film. A non-porous single layer adhesion barrier is least likely to allow adhesions to penetrate through to adjacent tissue.

An adhesion barrier film made of the above-described materials can be made by standard polymer film forming techniques, e.g., compression of copolymer resin between heated polytetrafluoroethylene (PTFE) coated plates. Other film forming techniques are described in, e.g., the Encyclopedia of Polymer Science and Engineering, Vol. 12, pp. 204–210 (1988), the contents of which are incorporated herein by reference. The thickness of the film can range from about 0.1 mil to about 100 mil, and is most preferably about 1 mil to about 3 mil.

In another embodiment, a single layer foam bioabsorbable surgical adhesion barrier made of the above described materials can be made in accordance with known foam forming techniques such as those disclosed in U.S. Pat. Nos. 3,902,497 or 5,102,983, whose contents are incorporated herein by reference. The foam may be sliced and/or cut to desired thickness and configuration before surgical use. The thickness of the foam layer can range from about 0.1 mil to about 100 mil, and is most preferably about 1 mil to about 3 mil.

A single layer bioabsorbable surgical adhesion barrier according to the present invention is flexible, resilient and conformable to the shape of underlying tissue. Films and foams constructed from the above-described polymers are well suited for draping over and conforming to areas of surgical wounds or injury and are especially well suited for endoscopic surgery, e.g., laparoscopy.

In another aspect of the present invention, a surgical adhesion barrier is formed from two layers, i.e., a bioabsorbable layer superimposed on a non-absorbable layer. The non-absorbable layer is flexible and provides support and shape. The non-absorbable layer can be made from biocompatible materials which are formed into a mesh, web, foam, woven fabric, non-woven fabric, porous film or non-porous film.

Biocompatible materials which are suitable for forming the non-absorbable layer are well-known and include fluoropolymers, polyesters, e.g polyethylene terephthalate or polybutylene terephthalate, polyetherimide esters, polyolefins, polyamides, polybutesters, and/or copolymers and/or blends of the same. These materials are exemplified by polytetrafluoroethylene (PTFE), silicone rubbers, urethanes, polyethylene, polypropylene, polyvinyl alcohol, polyvinyl chloride, cellulose, cellulose derivatives, fibroin, etc. Polypropylene is a preferred non-absorbable biocompatible material.

The non-absorbable layer can range from substantially non-porous to an open mesh. A non-porous non-absorbable layer substantially prevents the transmission of vapor, fluid or other substances from the wound site to the surrounding environment and, conversely, from the surrounding environment to the wound site. A porous film, matrix, mesh, web or fabric does permit such transmission. For reasons elaborated on below, a non-absorbable layer which permits transmission of vapor, fluid, or other substance may be desirable for use in aiding the healing process or in delivering a medicinal agent to the area of injury. Such a mesh material can promote the ingrowth of new tissue during the healing process. Methods of forming mesh, webs, woven fabrics, non-woven fabrics, matrices, foams, porous films and non-porous films from the above-noted materials are known to those with skill in the art.

The bioabsorbable layer of a two layer surgical adhesion barrier includes the same materials and forms described above in relation to a single layer bioabsorbable surgical adhesion barrier. The bioabsorbable layer according to the present invention may be in the form of mesh, web, woven-fabric, non-woven fabric, foam, matrix, or film. The thickness of each bioabsorbable layer can range from about 0.1 mil to about 100 mil, but preferably about 1 mil to about 3 mil. Non-porous films are preferred for use as the bioabsorbable layer in the present invention because adhesions are less likely to penetrate through to an underlying layer.

In a preferred embodiment of the two layer adhesion barrier, a bioabsorbable substantially non-porous layer is pressed onto a mesh (preferably about 12 inches×about 36 inches) constructed from polypropylene. The bioabsorbable layer is preferably made from either 1) a copolymer of about 20 mole percent glycolide and about 80 mole percent trimethylene carbonate or 2) a block copolymer having one block containing about 20 mole percent glycolide and about 80 mole percent trimethylene carbonate and another block containing about 20 mole percent glycolide and about 80 mole percent lactide wherein both blocks are present in equal weight ratios. In manufacturing a two layer surgical adhesion barrier according to the present invention a bioabsorbable layer is superimposed or affixed to a non-absorbable layer. For example, affixation may be accomplished by coating the bioabsorbable layer onto the non-absorbable layer. In one embodiment, the bioabsorbable polymer forming the bioabsorbable layer is melted and then coated on the non-absorbable mesh. Alternatively, the bioabsorbable polymer is dissolved in solvent and solution coated on to the mesh. The solvent is then evaporated by drying. The bioabsorbable layer may also be applied to the non-bioabsorbable layer by transfer coating techniques, such as these described in the Encyclopedia of Polymer Science pp. 377–382 (1985), the contents of which are incorporated herein by reference. Alternatively, a commercially available press machine is used to press a preformed film on to the mesh, or the polymer is calendared to form a film and then pressed onto the mesh. Techniques used for calendaring are well-known, e.g., techniques described in the Encyclopedia of Polymer Science and Engineering, Vol. 2, pp. 606–622 (1985), whose contents are incorporated herein by reference. The layers may also be joined by laminating the bioabsorbable layer to the non-absorbable layer. In lamination, the bioabsorbable layer may be applied to the non-absorbable layer by any method known to those with skill in the art, such as with an adhesive, for example, acrylic, silicone, polyphenolic bioadhesive, etc.

A two layer surgical adhesion barrier according to the present invention is flexible, resilient and conformable to the shape of underlying tissue. Such an adhesion barrier is well suited to be applied to a target site with minimally invasive techniques such as those involving endoscopy. After being positioned, two layer surgical adhesion barriers may optionally be sutured, stapled or otherwise fastened to the target site.

In another aspect of the present invention, a plurality of bioabsorbable layers are superimposed on a non-absorable layer in any of the aforementioned forms to form a surgical adhesion barrier. As above, the non-absorbable layer can be formed from biocompatible materials such as fluoropolymers, polyesters e.g. polybutylene terephthalate and polyethylene terephthalate, polyolefins, polyamides, polybutesters, polyetherimide esters, and/or copolymers and/or blends of the same. These materials are exemplified by polytetrafluoroethylene (PTFE), silicone rubbers, urethanes, polyethylene, polypropylene, polyvinyl alcohol, polyvinyl chloride, cellulose, cellulose derivatives, fibroin, etc. Polypropylene is a preferred non-absorbable layer.

Non-absorbable layers useful in this aspect of the present invention can range from the substantially non-porous to the open meshes described above. Biocompatible bioabsorbable materials useful in this aspect of the present invention include polymers and/or copolymers and/or blends of the aforementioned bioabsorbable materials.

Other examples of suitable biocompatible polymers are polyhydroxyalkyl methacrylates including ethylmethacrylate, and hydrogels such as polyvinylpyrrolidone, polyacrylamides, etc. Other suitable bioabsorbable materials are biopolymers which include collagen, gelatin, alginic acid, chitin, chitosan, fibrin, hyaluronic acid, dextran and polyamino acids. Any combination, copolymer, polymer or blend thereof of the above examples are contemplated for use according to the present invention. Such bioabsorbable materials may be prepared by known methods.

A surgical adhesion barrier having a plurality of bioabsorbable layers can be formed by superimposing a first bioabsorbable layer on a nonabsorbable layer by any of the techniques which are described in relation to forming a two layer surgical adhesion barrier. A second bioabsorbable layer is then superimposed or affixed to the first bioabsorbable layer by such means as are described above. In this manner, a third, fourth, fifth, etc. bioabsorbable layer may be successively incorporated into the surgical device of the present invention. Alternatively, a first bioabsorbable layer may be superimposed on a second bioabsorbable layer to form a two layer bioabsorbable composite. Optionally, a third, fourth, fifth, etc. layer can be added successively to form a multi-layer bioabsorbable composite which is then superimposed on a non-absorbable layer by such means that are described above.

The physical form of each successive bioabsorbable layer in all above and below-described embodiments and aspects of the present invention can vary. For example, the outermost bioabsorbable layer can be a film and an adjacent bioabsorbable layer can be, e.g., a mesh, film, foam or non-woven fabric. Any number of such combinations are contemplated by the present invention.

In another aspect of the present invention, at least one bioabsorbable non-woven fabric layer is superimposed or affixed to at least one bioabsorbable layer which may be a film, mesh, web, foam, woven fabric or other non-woven fabric. The bioabsorbable materials used to form the non-woven fabric layer(s) include all known bioabsorbable materials and combinations of such materials capable of being formed into fibers including those previously referred to herein. Methods for making non-woven fabrics are generally known in the art.

Figure 1:
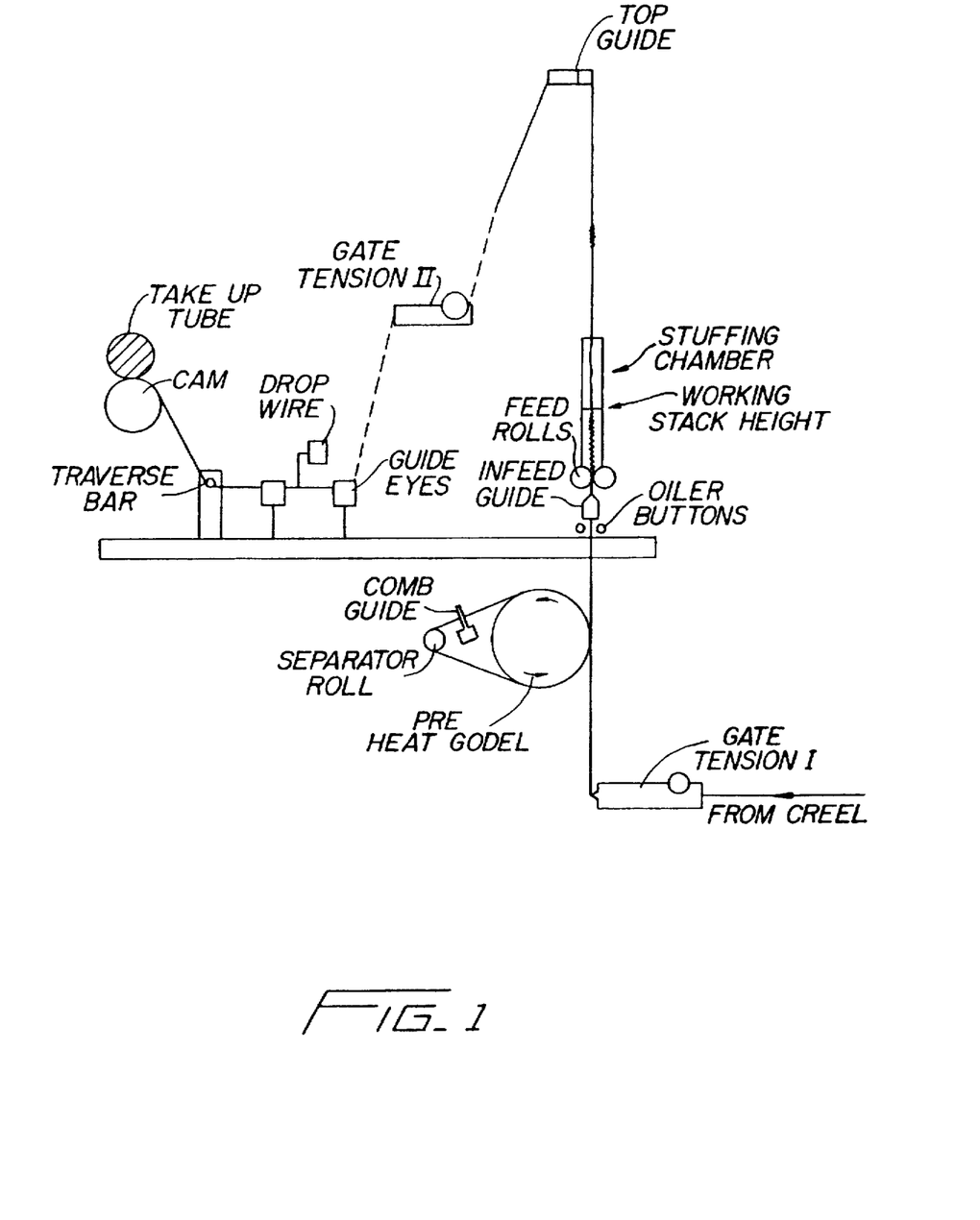
FIG. 1 is a diagram of a stuffer box/crimper suitable for processing filaments used in the manufacture absorbable non-woven fabric for use in the present invention.

Preferably, a low density non-woven bioabsorbable fabric is used to carry out the present invention. In one preferred embodiment, the low density bioabsorbable non-woven fabric is manufactured from a 92.5/7.5 (mole percent) glycolide/lactide polymer yarn. The polymer is spun and drawn into a 69 filament 14 ply multifilament yarn of about 1.6 denier per filament. The 14 plyes are combined together by using a creel and a constant speed winder to prepare 1541 denier plied yarn. The yarn is crimped into a stuffer box according to the preferred specifications shown in Table I, below, with reference to FIG. 1.

TABLE I

| Crimping Stufferbox Crimper | |
|---|---|
| Conditions | |
| No. of yarn ends feeding from creel: | 1 |
| Total Yarn denier: | 1545 (14 ply × 69 filaments/yarn × 1.6 dpf) |
| Gate Tension 1 Setting: | 4 |
| Godet Setup: | |
| No. of wraps on the pre-heat godet: | 19 |
| Pre-heat Godet Set Temp: | 108° |
| Pre-heat Godet Indicating Temp: | 110° |
| Speed | 31 meters/minute |
| Infeed Gears | 48 × 18 |
| (adjust's infeed yarn tension): | |
| Stuffer Chamber Setup: | |
| Column Temp. Set Point (back only): | 96° C. |
| Indicating Temp. of Column: | 99° C. |
| 8" glass column front | |
| Working Stack Height in Column: | 6.5" to 7.5" |
| Take up gears | 26 × 15 |
| (adjusts column stack height): | |
| Gate Tension II Setting: | 0.5 |
| Crimp Analysis: | |
| Average No. of Crimps/inch: | 23.7 |
| Range (Min./Max.) | 16/36 |

The crimped yarn is cut into staples having fibers ranging from about 2–2.50 inches with an average length of about 2.25 inches. The staples are then carded to form a web. Prior to web formation, the staple fibers are passed through the card once to open the fibers. After opening, approximately 55 grams of opened fibers are used to produce a carded web having a basis weight of approximately 100 g/m$^2$, with dimensions of about 0.22 m×about 1.9 m. The carding specifications are shown in Table II.

TABLE II

| Carding 12" metallic card with variable speed control | |
|---|---|
| Card Conditions | |
| Main Cylinder Speed: | 186–188 rpms |
| Worker Cylinders: | 21–22 rpms |
| Stripper Cylinders: | 335 rpms |
| Take-off Apron: | 53 rpms |

From about one to about four carded web layers are then cross-lapped and needle-punched twice to form the bioabsorbable non-woven fabric. All web layers are combined during the first needle-punch pass. The second needle-punch pass is "dry", i.e., no webs are added. The first needle-punch pass involves the face fabric direction with about 320 needle penetrations per square inch to a depth of about 4 mm. The second needle-punch pass involves the back fabric direction with about 320 needle penetrations per square inch to a depth of about 8 mm. Certain other needling parameters are shown in Table III.

TABLE III

| Needling: 12" James Hunter Fiberlocker | |
|---|---|
| Needling Parameters | |
| Needle Type: | Groz Beckert, GB 30's 15 × 18 × 36 × 3 Barb Types: F333, G92919 |
| Needling Rate: | 120 strokes/minute |
| Needling Board Density: | 46 needles/linear inch |

When using two carded web layers, the resulting non-woven fabric is about 0.5 meters wide, less than about 2.5 mm thick and has a density of between about 0.05 g/cu.cm and about 0.10 g/cu.cm. Preferably, the density is between about 0.065 g/cu.cm and about 0.085 g/cu.cm. The basis weight of the fabric depends on the number of carded web layers needled together. Each carded web layer has a basis weight of between about 50 g/sq.m and about 100 g/sq.m. Preferably, the carded web layer basis weight is about 80 g/sq.m. The basis weight of a two layer fabric, for example, is between about 100 g/sq.m and about 200 g/sq.m and preferably about 160 g/sq.m. optionally, the fabric can be coated or filled with various storage stabilizing agents, such as those disclosed in commonly assigned U.S. Pat. No. 5,032,429, the contents of which are incorporated herein by reference. Such storage stabilizing agents can include, for example, glycerol and calcium lactate.

According to the present invention, the thickness of the non-woven fabric can range from about 0.5 mm to about 5 mm, and is preferably about 1.75 mm to about 3 mm, but most preferably about 2.5 mm. In another preferred embodiment, the mole percent ratio of glycolide to lactide is about 20:80, and most preferably about 18:82, and can be manufactured in a manner as described above.

The non-woven fabric layer(s) are superimposed or affixed to at least one bioabsorbable layer of foam, film, mesh, web, woven fabric or other non-woven fabric. Bioabsorbable foam layers discussed previously in relation to single layer bioabsorbable surgical adhesion barriers herein are suitable for superimposing or affixing to the non-woven fabric layer. Bioabsorbable meshes, webs, woven fabrics or other non-woven fabrics can be manufactured by known techniques and also superimposed or affixed to the non-woven fabric layer(s) in accordance with the present invention. In a preferred embodiment, the non-woven fabric is superimposed on or affixed to a bioabsorbable film. Bioabsorbable film made of any of the above-described bioabsorbable polymers, copolymers, or blends thereof can be manufactured by standard polymer film forming techniques, e.g. compression of polymer resin between PTFE coated platens. Other film forming techniques are described in, e.g., the Encyclopedia of Polymer Science and Engineering, Vol. 12, pp. 204–210 (1988). In a most preferred embodiment the bioabsorbable polymer is dissolved in a suitable solvent, e.g., methylene chloride, acetone, etc., to form a mixture of desired viscosity which is coated onto release means such as release paper or the like to form a film. During evaporation of the solvent, a bioabsorbable non-woven fabric layer(s) is placed on the wet film. The film then adheres to the non-woven fabric and the release means is removed. The film may range from 0.1 mil to 4 mil and is preferably about 2 mil.

The bioabsorbable foam or film may be fabricated from any of the well known bioabsorbable polymers used in medicine. A preferred bioabsorbable polymer for use in the foam or film is described above in accordance with a surgical adhesion barrier constructed from a single layer of bioabsorbable material, i.e., copolymers of carbonates and at least one other bioabsorbable material. A highly preferred bioabsorbable polymer for use in the foam or film is fabricated from block copolymers having about 50% by weight of an "A" block comprising about 40 mole percent glycolide and about 60 mole percent trimethylene carbonate and about 50% by weight of a "B" block comprising about 20 mole percent lactide and about 80 mole percent glycolide. Another highly preferred bioabsorbable polymer is fabricated from block copolymers having about 20% by weight of an "A" block comprising about 20 mole percent glycolide and about 80 mole percent trimethylene carbonate and about 80% by weight of a "B" block comprising about 20 mole percent glycolide and about 80 mole percent lactide.

As above, additional bioabsorbable layers may be affixed or superimposed to form surgical adhesion barriers of greater than two layers. The same techniques for affixing or superimposing a bioabsorbable layer to a nonabsorbable layer described above are applicable to any of the layers involving non-woven bioabsorbable fabric. The successive layers may comprise differing chemical compositions and/or physical forms to yield adhesion barriers of markedly different characteristics depending on intended use.

In all the above aspects and embodiments, the rate of bioabsorption of each bioabsorbable layer can be varied by changing the chemical make up and/or thickness of each successive layer. Various bioabsorbable polymers, copolymers and/or blends thereof are known to have different rates of absorption. For example, bioabsorbable polymers having a high degree of crystallinity are absorbed less rapidly than bioabsorbable polymers having relatively higher amounts of amorphous regions. Thus, rates of bioabsorption can be engineered to fit particular needs. In this way, an outermost bioabsorbable layer can be constructed to slowly biodegrade and, when it does, adhesions which have formed between the outer layer and surrounding tissue fall away. Any slower forming adhesions which may have adhered through the outermost layer to an inner layer would then be disconnected by the absorption of a rapidly biodegrading inner layer. Alternatively, a rapidly bioabsorbed outer layer would act as the first line of defense against rapidly forming adhesions and a slower bioabsorbed inner layer would prevent the attachment of late forming adhesions.

Optionally, one or more medicinal agents may be interposed between one or more layers of a surgical device according to the present invention.

The present invention provides a versatile scheduled release medicinal agent(s) delivery system. For example, a bioabsorbable layer that has been engineered for rapid absorption releases any medicinal agents contained between such layer and an adjacent layer within a relatively fast time frame. If the next bioabsorbable layer is engineered to be absorbed more slowly any medicinal agent contained between such layer and a next adjacent layer will be released within that time. Thus, a schedule of therapy is created with delivery at two distinct points in time, i.e., first, following implantation and absorption of the rapidly bioabsorbable layer, and second, after absorption of the more slowly absorbed layer.

Optionally, one or more medicinal agents may be mixed or ground into the above-mentioned bioabsorbable polymeric materials prior to formation of a coating or layers. See, e.g., U.S. Pat. No. 3,991,766. In this manner, the medicinal agent is slowly released as the bioabsorbable layer is absorbed. The non-absorbable layer can also be manufactured such that a medicinal agent is integrally incorporated therein and diffuses or is transported to the wound site therefrom. For example, a medicinal agent can be co-extruded with a polymer such as polypropylene to form fibers containing the medicinal agent.

The term "medicinal agent", as used herein, is meant to be interpreted broadly and includes any substance or mixture of substances which may have any clinical use in medicine. Thus medicinal agents include drugs, enzymes, proteins, peptides, glycoproteins, or diagnostic agents such as releasable dyes which may have no biological activity per se.

Examples of classes of medicinal agents that can be used in accordance with the present invention include antimicrobials, analgesics, antipyretics, anesthetics, antiepileptics, antihistamines, anti-inflammatories, cardiovascular drugs, diagnostic agents, sympathomimetic, cholinomimetic, anti-muscarinics, antispasmodics, hormones, growth factors, muscle relaxants, adrenergic neuron blockers, anti-neoplastics, immunosuppressants, gastrointestinal drugs, diuretics, steroids and enzymes. It is also intended that combinations of medicinals can be used in accordance with the present invention.

Thus, in one embodiment of the present invention focal delivery and application of a medicinal agent to the wound site is achieved. Focal application can be more desirable than general systemic application in some cases, e.g., chemotherapy for localized tumors, because it produces fewer side effects in distant tissues or organs and also concentrates therapy at intended sites. Focal application of growth factors, anti-inflammatories, immune system suppressants and/or antimicrobials by a the anti-adhesion device of the present invention is an ideal drug delivery system to speed healing of a wound or incision.

A post surgical anti-adhesion device or structure of the present invention is generally used in the form of a sheet of a desired size and shape. A surgeon may cut a custom shape from preformed sheets to suit particular applications. After the device is shaped for a suitable fit, the flexible nature of the device enables the surgeon to conform the device to fit around the area of injury. In one embodiment, the device is formed into a strip which wraps around the organ, e.g., an intestine, to prevent formation of adhesions. An anti-adhesion device according to the present invention can incorporate ties or straps which connect to the device and which are used to tie or otherwise secure the device to an area of injury. It is further contemplated that the anti-adhesion devices of the present invention may be affixed to the wound site by surgical fasteners or sutures. The flexible nature of the present anti-adhesion device allows the device to flex and bend along with normal movements of the body without being overly restrictive.

All embodiments of surgical adhesion barriers or structures as described herein are well-suited for application by techniques involving endoscopy. Endoscopic surgical procedures involve the use of cannulas or tubes which provide narrow openings into a body and allow minimally invasive access to surgical targets. In laparoscopic procedures, surgery is performed in the interior of the abdomen through small tubes inserted therein. Endoscopes are frequently used as viewing devices inserted through the cannulas which allow surgeons to see the interior of the body.

Certain endoscopic and laparoscopic procedures may require that the surgical region be insufflated. Accordingly, any instrumentation inserted into the body should be substantially sealed to ensure that gases do not enter or exit the body through the incision. Moreover, endoscopic and laparoscopic procedures often require the surgeon to operate on organs, tissues and/or vessels far removed from the incision. Thus, instruments used in such procedures are typically long and narrow while being functionally controllable from a proximal end of the instrument.

In accordance with the present invention an apparatus for deploying and positioning any of the adhesion barriers or structures disclosed herein may be inserted through a cannula and deposited at a target site. Once the barrier is positioned as desired, it may optionally be sutured, stapled or otherwise fastened to the target site with instruments designed to be inserted through a cannula.

In order that those skilled in the art may be better able to practice the present invention, the following examples are given as an illustration of the preparation and superior characteristics of the anti-adhesion devices of the present invention. It should be noted that the invention is not limited to the specific details embodied in the examples.

EXAMPLE 1

Copolymer of Glycolide/Trimethylene Carbonate (Polymer I)

A 20/80 mole percent glycolide/trimethylene carbonate copolymer was prepared in a reactor by combining previously dried 53.13 grams of glycolide and 186.87 grams of trimethylene carbonate and polymerizing at 160° C. for 24 hours in the presence of 0.05 grams of stannous octoate. The polymer was extruded from the reactor and post treated to remove any residual monomer present in the polymer. The inherent viscosity of the polymer was 0.9.

EXAMPLE 2

Copolymer of Glycolide/Trimethylene Carbonate/ Lactide (Polymer II)

A block copolymer having one block containing 20 mole percent glycolide and 80 mole percent trimethylene carbonate and another block containing 20 mole percent glycolide and 80 mole percent lactide, wherein both blocks are present in equal weight ratios was prepared in a reactor. 553.4 grams of glycolide and 1946.6 grams of trimethylene carbonate were added to the reactor along with 1.0 grams of stannous octoate and dried under vacuum in the reactor for about 16 hrs. After drying, the reactants were heated at 150° C. and polymerized for about 24 hrs. At this stage 419.1 grams of dried glycolide and 2080.9 grams of Lactide were added and continued polymerizing of additional 24 hrs. The polymer is extruded and post treated to remove any residual monomers present in the polymer. The inherent viscosity of this polymer was 1.32.

EXAMPLE 3

Copolymer of Glycolide/Trimethylene Carbonate/ Lactide (Polymer III)

A block copolymer having 50% by weight of one block containing 40 mole percent glycolide and 60 mole percent trimethylene carbonate and 50% by weight of another block containing 20 mole percent glycolide and 80 mole percent lactide was prepared in a reactor. 646.7 grams of glycolide and 853 grams of trimethylene carbonate were added to the reactor along with 0.6 grams of stannous octoate and dried under vacuum in the reactor for about 24 hours at 160° C. At this stage 251 grams of glycolide and 1248 grams of lactide were added and polymerized for an additional 24 hours at 170° C. The polymer was extruded and post treated to remove any residual monomers present in the polymer. The inherent viscosity of this polymer was in the range of 0.4–0.8 dl/g.

EXAMPLE 4

Copolymer of Glycolide/Trimethylene Carbonate/ Lactide (Polymer IV)

A block copolymer having 20% by weight of one block containing 20 mole percent glycolide and 80 mole percent trimethylene carbonate and 80% by weight of another block containing 20 mole percent glycolide and 80 mole percent lactide was prepared in a reactor. 132.8 grams of glycolide and 467.2 grams of trimethylene carbonate were added to the reactor along with 0.6 grams of stannous octoate and dried under vacuum in the reactor for about 24 hours. At this stage 402 grams of glycolide and 1998 grams of lactide were added and polymerized for an additional 24 hours. The polymer was extruded and post treated to remove any residual monomers present in the polymer. The inherent viscosity of this polymer was of 0.6 to 1.1 dl/g.

EXAMPLE 5

Construction of Multilayer Adhesion Barrier

Polymer I, made in accordance with Example 1, was pressed into a film by means of a vacuum press supplied by Technical Machine Products, Cleveland, Ohio, a standard commercial press having PTFE coated platens. The temperature of the platens was maintained at about 130° C. The platens were pressed together at a load of about 25,000 pounds for about 12 minutes. The resulting film was then removed from the press.

To bond the polymer film to a polypropylene mesh, the film was placed against the mesh and pressed together by the PTFE coated platens of a vacuum press supplied by Technical Machine Products, Cleveland, Ohio. The temperature of the platens was maintained at about 65° C. and the platens were pressed together at a load of about 1000 pounds for about 5 minutes. The multilayer adhesion barrier was then removed from the press.

EXAMPLE 6

Construction of Multilayer Adhesion Barrier

Polymer II, made in accordance with Example 2,is pressed into a film in a manner similar to that described in Example 3 except that the platens were heated to a temperature of about 190° C. and pressed together at a load of about 3000 pounds.

To bond the polymer film to a polypropylene mesh, the film was placed against the mesh and pressed together by the PTFE coated platens of a vacuum press supplied by Technical Machine Products, Cleveland, Ohio. The temperature of the platens was maintained at about 120° C. and the platens were pressed together at a load of about 3000 pounds for about 5 minutes. The resulting multilayer adhesion barrier was then removed from the press.

EXAMPLE 7

Construction of Bioabsorbable Non-Woven Fabric

A copolymer of about 18 mole percent glycolide and about 82 mole percent lactide was spun and drawn into a 40 filament 14 ply multifilament yarn. The plies were combined (1120 denier total) and crimped by stuffer box crimper. The crimped yarn was cut into staples of about 2 inches. The staple fibers were opened and carded on a carding machine and converted to a web having a basis weight of approximately 100 g/m². Two web layers were needled together to form non-woven fabric (200 g/m²) which was washed in water for 5 minutes and dried in vacuum. The dried fabric was post treated at 90° C. for 16 hours and then platen pressed at 90° C. for 12 seconds with 0.20 inch shims. The pressed non-woven fabric was postwashed in water for 5 minutes and dried in vacuum to yield a bioabsorbable non-woven fabric product.

EXAMPLE 8

Construction of Multilayer Adhesion Barrier

Polymer III, made in accordance with Example 3, was dissolved in methylene chloride at room temperature while stirring until the mixture contains about 30 to about 50% and preferably about 35% solids. Transfer coating equipment was utilized to form an adherent bond between a non-woven fabric made in accordance with Example 5 and a film described herein. The line speed ran at 6 feet per minute. Oven temperatures were read at about 112° F. in the first zone, about 107 in the second zone and about 110° F. in the third zone. The web temperature was about 119° F. The polymer mixture, with a viscosity of about 500 CPS is coated onto moving release paper to form an approximately 2 mil film. The bioabsorbable non-woven fabric was placed onto the wet film. A light weight card board was placed on the fabric to maintain good adherent contact with the film. The film and fabric were then passed through the ovens. The solvent evaporated and a dry product having the film and fabric in adherent contact resulted. The release paper was peeled off the film side of the adhesion barrier. Alternatively, two layers of 1 mil film can be applied separately and adhered. By applying multiple layers, irregularities in the film layer, such as small holes, are less likely to be present in the final product.

EXAMPLE 9

Construction of Multilayer Adhesion Barrier

An approximately 2 mil film of polymer III, made in accordance with Example 8 is produced on release paper without non-woven fabric. After drying, the film was cut to desired, size and placed in contact with the film side of the adhesion barrier made in accordance with Example 8. The films inherently adhere to each other and a trilayer adhesion barrier was prepared with a manual laminator by feeding the film and the two-layer adhesion barrier into the laminator between movable rollers.

EXAMPLE 10

Implantation of Polymer I Adhesion Barrier

Twelve female Sprague-Dawley rats weighing between 255–250 gm each were monitored for at least one week prior to surgery to insure good health and stability. The animals were anesthetized with intraperitoneal sodium pentobarbital and their abdomens prepared for surgery. The abdominal cavity was exposed through a midline incision. On the abdominal wall overlying the cecum, a 1 cm×2 cm area of parietal peritoneum was carefully excised from the abdominal wall, removing a thin layer of muscle along with the peritoneum.

The cecum was elevated and isolated by moist gauze. The proximal end of the cecum was emptied of its contents. A 1 cm×2 cm area on the anterior surface of the proximal end of the cecum was gently abraded by rubbing 10 times with dry gauze. The cecum was then scraped with a scalpel blade to cause minute petechial hemorrhages. The cecal abrasion was left exposed for 15 minutes. After 15 minutes, the cecal abrasion and the abdominal wound were blotted with a gauze sponge to gently remove any excess blood and ensure complete hemostasis. Placement of these two wounds together normally leads to reproducible formation of an adhesion.

A 2 cm×3 cm film of Polymer I approximately 7 mil thick made in a manner according to Example 3 was placed between the wounds before they were placed in contact and the abdomen closed. The procedure was repeated on all twelve rats.

Seven days following surgery, the animals peritoneum was evaluated for the development of an adhesion between the peritoneal defect and the cecal surface. Examination of the wound site revealed that one of twelve rats had developed an adhesion.

EXAMPLE 11

Implantation of Polymer II Adhesion Barrier

Polymer II in accordance with Example 2 was formed into a single layer film approximately 7 mil thick and implanted in a manner similar to that described in Example 5. Examination of the wound site after seven days revealed that one of twelve rats had developed an adhesion.

EXAMPLE 12

Implantation of Polymer I/Polypropylene Mesh Adhesion Barrier 1 cm×2 cm pads of SURGIPRO® polypropylene mesh (commercially available from U.S. Surgical Corp.) coated with a film of Polymer I were implanted into fifteen rats in a manner similar to that described in Example 5 except that certain different groups of the rats were analyzed at three specified time intervals: 7, 31 and 55 days, respectively. At day 7 one of five rats developed a retroperitoneal fat adhesion; no cecal adhesions were observed. At day 21 two of five rats were observed with cecal adhesions. At day 55 none of five rats were observed with cecal adhesions. In sum, three of fifteen rats were observed with cecal adhesions at the wound site.

EXAMPLE 13

Implantation of Polymer II/Polypropylene Mesh Adhesion Barrier 1 cm×2 cm pads of SURGIPRO® polypropylene mesh (commercially available from U.S. Surgical Corp.) coated with a film of Polymer II were implanted into fourteen rats in a manner similar to that described in Example 12. At day 7 none of five rats were observed with adhesions. At day 21 one of five rats was observed with a cecal adhesion. At day 55 none of four rats were observed with cecal adhesions. In sum, one of fourteen rats was observed with cecal adhesions at the wound site.

EXAMPLE 14

Implantation of Polymer II/Polypropylene Mesh Adhesion Barrier 2 cm×3 cm pads of a 2 mil film of Polymer II bonded to Surgipro® polypropylene mesh (commercially available from U.S. Surgical Corp.) were implanted into thirty-six rats in a manner similar to that described in Example 10 except that the pads were sutured to the abdominal wall using size 7/0 polypropylene suture in each corner of the pad and that wound cites of three groups of twelve rats were analyzed for adhesions at 7, 14 and 21 days, respectively, following implantation. After 7, 14 and 21 days none of the rats were observed with cecal adhesions at the wound site.

EXAMPLE 15

Implantation of Polymer II/Polypropylene Mesh Adhesion Barrier 2 cm×3 cm pads of a 4 mil film of Polymer II bonded to Surgipro® polypropylene mesh (commercially available from U.S. Surgical Corp.) were implanted into twelve rats in a manner similar to that described in Example 14. After 7, 14 and 21 days none of the rats were observed with cecal adhesions at the wound site.

EXAMPLE 16

Implantation of Polymer II Film Adhesion Barrier 2 cm×3 cm pads of a 2 mil film of Polymer II were implanted into thirty rats in a manner similar to that described in Example 14. After 7 days the incidence of cecal adhesions was about 25% in twelve rats. Two of the cecal adhesions are believed to have been caused by technical error. At days 14 and 21 about an 11% incidence of cecal adhesions was observed, respectively, in two groups of nine rats.

EXAMPLE 17

Implantation of Polymer II Adhesion Barrier 2 cm×3 cm pads of a 4 mil film of Polymer II were implanted into thirty-six rats in a manner similar to that described in Example 14. There were no cecal adhesions observed at day 7. At days 14 and 21, about an 8% incidence of adhesions was observed, respectively, in two groups of twelve rats.

EXAMPLE 18

Implantation of Polymer II/Polypropylene Mesh Adhesion Barrier

Six Yorkshire gilts weighing between 38 and 46 kg received standard dosage, intramuscular injections of antibiotic and were anesthetized. A midline celiotomy incision was made and, on both sides of the body wall, an approximate 3×3 cm section of the peritoneum, the internal abdominal fascia and the abdominal wall muscle were removed. Each partial thickness defect was repaired with a SURGIPRO® polypropylene mesh (U.S. Surgical Corp.) coated with a film of Polymer II. A total of twelve abdominal wall defects were created and repaired, two per animal.

The abdominal wall and defect repair sites were examined for the type and extent of adhesions after two weeks. Adhesions were observed at three of the twelve wound sites.

COMPARATIVE EXAMPLE 1

2 cm×3 cm Hyaluronic acid pads (commercially available from Med Chem) were implanted in seventeen rats in a manner similar to that described in Example 10. Examination of the wound site after seven days revealed that twelve of seventeen rats developed adhesions.

COMPARATIVE EXAMPLE 2

3 cm diameter Hylan NWM discs (commercially available from Biomatrix, Inc.), circulars disc containing hyaluronic acid, were implanted in eleven rats in a manner similar to that described in Example 10. Examination of the wound site after seven days revealed that two of eleven rats developed adhesions.

COMPARATIVE EXAMPLE 3

Hylan solution (commercially available from Biomatrix, Inc.), a hyaluronic acid gel, was applied to both wound surfaces of twelve rats caused in a similar manner as the wound surfaces created in Example 10. Seven of twelve rats developed adhesions at the wound site.

COMPARATIVE EXAMPLE 4

3% methylcellulose solution was applied to both wound surfaces of eleven rats caused in a similar manner as the wound surfaces created in Example 10. Five of eleven rats developed adhesions at the wound site.

COMPARATIVE EXAMPLE 5

1 cm×2 cm pads of uncoated SURGIPRO® polypropylene mesh (commercially available from U.S. Surgical Corp.) were implanted into fifteen rats in a manner similar to that described in Example 10 except that certain of the rats were analyzed at three specified time intervals: at 7, 21, and 55 days, respectively. It is believed that one of the fifteen rats was mislabeled and discounted in the group analyzed at 7 days; at day 7 three of four rats developed cecal adhesions; at day 21 three of five rats developed cecal adhesions; at day 55 three of five rats developed cecal adhesions. In sum, nine of fourteen remaining rats developed cecal adhesions at the wound site.

COMPARATIVE EXAMPLE 6

1 cm×2 cm pads of SURGIPRO® polypropylene mesh (commercially available from U.S. Surgical Corp.) coated with film of hydroxyethylmethacrylate (HEMA) were implanted into fifteen rats in a manner similar to that described in Comparative Example 10. At day 7, one of five rats was observed with a cecal adhesion and three of the five rats were observed with retroperitoneal fat adhesions. At day 21 two of five rats were observed with cecal adhesions. At day 55 two of five rats were observed with cecal adhesions. In sum, five of fifteen rats were observed with cecal adhesions at the wound site.

COMPARATIVE EXAMPLE 7

Pads of Marlex® polypropylene mesh (commercially available from C.R. Bard., Inc.) were implanted into six defect sites created in gilts in a manner similar to that described in Example 18. Four of six defect sites were observed with adhesions.

COMPARATIVE EXAMPLE 8

Pads of Gore-Tex® mesh (commercially available from W.L. Gore & Co.) were implanted into six defect sites created in gilts in a manner similar to that described in Example 18. Three of six defect sites were observed with adhesions.

COMPARATIVE EXAMPLE 9

Pads of Interceed® oxidized regenerated cellulose (commercially available from Ethicon, Inc.) were implanted into six defect sites created in gilts in a manner similar to that described in Example 18. Two of six defect sites were observed with adhesions.

COMPARATIVE EXAMPLE 10

Six defect sites were created in gilts in a manner similar to that described in Example 18, but no implant was used at the defect site, i.e., the defects were unrepaired. Two of six defect sites were observed with adhesions.

COMPARATIVE EXAMPLE 11

2 cm×3 cm pads of Marlex® polypropylene mesh (commercially available from C.R. Bard, Inc.) were implanted into twelve rats in a manner similar to that described in Example 10 except that the pads were sutured to the abdominal wall using size 7/0 polypropylene suture in each corner of the pad. The stitches were placed so that the knots were under the sample and not exposed. After seven days, all twelve rats were observed with adhesions at the wound site.

COMPARATIVE EXAMPLE 12

2 cm×3 cm pads of Surgipro® polypropylene mesh (commercially available from U.S. Surgical Corp.) were implanted into twelve rats in a manner similar to that described in Comparative Example 11. After seven days, all twelve rats were observed with adhesions at the wound site.

COMPARATIVE EXAMPLE 13

2 cm×3 cm pads of Interceed® oxidized regenerated cellulose (commercially available from Ethicon, Inc.) were implanted into twelve rats in a manner similar to that described in Comparative Example 11. After seven days, all twelve rats were observed with adhesions at the wound site.

COMPARATIVE EXAMPLE 14

2 cm×3 cm pads of Gore-Tex® soft tissue patch (commercially available from W.C. Gore & Co.) were implanted into twelve rats in a manner similar to that described in Comparative Example 11. After seven days, eight of twelve rats (about 67%) were observed with adhesions at the wound site.

Comparative Examples 7–14 also included observations of adhesions which are considered to be less important than cecal adhesions. Adhesions of lesser importance are categorized herein as Type 1, Type 2 and Type 3. Type 1 include fat, liver, or intestines adhered to the face of the test surface. Type 2 include fat, liver, or intestines adhered to a free edge of a test surface or to suture knots. Type 3 include adherence of the cecal defect to peritoneal wall caudal or lateral to the test site. The results of the observations relating to adhesions of lesser importance are summarized in Table I.

TABLE I

Incidence of adhesions other than the cecum adhering to the overlying test material.

| | INCIDENCE OF OTHER ADHESIONS (APPROXIMATE %) | | | | | | | | |
|---|---|---|---|---|---|---|---|---|---|
| | DAY 7 | | | DAY 14 | | | DAY 21 | | |
| TEST MATERIAL | Type 1 | Type 2 | Type 3 | Type 1 | Type 2 | Type 3 | Type 1 | Type 2 | Type 3 |
| SURGIPRO | 100 | 100 | 0 | N/A | | | N/A | | |
| MARLEX | 100 | 100 | 0 | | | | | | |
| INTERCEED | 92 | * | 0 | | | | | | |
| GORE-TEX | 75 | 58 | 8 | | | | | | |
| SURGIPRO + 2 mil film | 0 | 100 | 33 | 100 | 42 | 33 | 92 | 17 | 42 |
| SURGIPRO + 4 mil film | 0 | 100 | 25 | 91 | 9 | 18 | 91 | 36 | 18 |
| 2 mil film | 0 | 92 | 25 | 0 | 78 | 11 | 0 | 89 | 22 |
| 4 mil film | 0 | 83 | 17 | 0 | 75 | 0 | 0 | 100 | 33 |

* Type 2 adhesions were not possible for Interceed since its edges were the same as its surface and the material was not sutured to the peritoneal defect.

The principles, preferred embodiments and modes of operation of the invention have been described in the foregoing specification. The invention which is intended to be protected herein, however, is not to be construed as limited to the particular forms disclosed, since they are to be regarded as illustrative rather than restrictive. Modifications and variations of the present invention are possible in light of the above teachings. It is therefore to be understood that changes may be made in particular embodiments of the invention described which are within the full intended scope of the invention as defined by the claims.

What is claimed is:

1. A method for reducing occurrence of post-surgical adhesions comprising placing, at a site of surgical trauma, a biocompatable adhesion barrier which includes:
   a. about 10 to about 90% by weight of a block copolymer having at least one block of a bioabsorbable copolymer having greater than 50 mole percent of trimethylene carbonate; and
   b. about 10 to about 90% by weight of the block copolymer having at least another block of a bioabsorbable copolymer having greater than 50 mole percent of lactide; and reducing occurrence of post-surgical adhesions.

2. A method for endoscopic minimization of post-surgical adhesions comprising:
   (i) providing a biocompatable surgical structure including at least two bioabsorbable layers superimposed on a nonbioabsorbable layer, at least one of said bioabsorbable layers including a block copolymer wherein:
      a. about 10 to about 90% by weight of the block copolymer includes at least one block formed from a copolymer having greater than 50 mole percent of trimethylene carbonate; and
      b. about 10 to about 90% by weight of the block copolymer is another block formed from a copolymer having greater than 50 mole percent of lactide;
   (ii) inserting said surgical structure into a body cavity through a cannula;
   (iii) super imposing said surgical structure over a wound site; and
   (iv) thereby causing minimization of post-surgical adhesions.

3. A method for endoscopic minimization of post-surgical adhesions in endoscopic surgery comprising:
   (i) providing a biocompatable post-surgical adhesion barrier including at least two bioabsorbable layers wherein one of said layers is a bioabsorbable non-woven fabric and one of said layers is a bioabsorbable layer of a block copolymer, wherein:
      a. about 10 to about 90% by weight of the block copolymer is at least one block formed from a copolymer having greater than 50 mole percent of trimethylene carbonate; and
      b. about 10 to about 90% by weight of the block copolymer is at least another block formed from a copolymer having greater than 50 mole percent of lactide;
   (ii) inserting the post-surgical adhesion barrier into a body cavity through a cannula;
   (iii) placing the post-surgical adhesion barrier over an area of trauma; and
   (iv) thereby causing minimization of post-surgical adhesions.

4. A method of preventing formation of post-surgical adhesions comprising:
   (i) providing a biocompatable surgical structure including at least two bioabsorbable layers wherein one of said layers is bioabsorbable non-woven fabric and one of said layers is a bioabsorbable layer of a block copolymer, wherein:
      a. about 10 to about 90% by weight of the block copolymer is at least one block formed from a copolymer having greater than 50 mole percent of trimethylene carbonate; and
      b. about 10 to about 90% by weight of the block copolymer is at least another block formed from a copolymer having greater than 50 mole percent of lactide;
   (ii) superimposing said surgical structure over a wound site; and
   (iv) thereby preventing formation of post-surgical adhesions.

5. A method of preventing formation of surgical adhesions according to claim 4 further comprising inserting said surgical structure into a patient's body through a cannula.

* * * * *